United States Patent [19]

Elliott et al.

[11] Patent Number: 4,999,043

[45] Date of Patent: Mar. 12, 1991

[54] TRIAZOLYLMETHYL TERT-BUTYL CARBINOL DERIVATIVES WHICH HAVE PLANT GROWTH REGULATING PROPERTIES

[75] Inventors: Raymond Elliott, Nr. Reading; John Dalziel, Binfield; Raymond L. Sunley, Twyford, all of England

[73] Assignee: Imperial Chemical Industries PLC, London, England

[21] Appl. No.: 307,174

[22] Filed: Feb. 6, 1989

Related U.S. Application Data

[63] Continuation of Ser. No. 892,363, Aug. 4, 1986, abandoned.

[30] Foreign Application Priority Data

Aug. 7, 1985 [GB] United Kingdom ............... 8519843
Feb. 18, 1986 [GB] United Kingdom ............... 8603952

[51] Int. Cl.$^5$ ............... A01N 43/653; C07D 249/08
[52] U.S. Cl. ............................................. 71/92; 71/76; 548/101; 548/267.8
[58] Field of Search ............... 71/76, 92; 548/101, 548/262, 267.8

[56] References Cited

U.S. PATENT DOCUMENTS

| 4,243,405 | 1/1981 | Balasubramanyan et al. ..... 548/262 |
| 4,414,210 | 11/1983 | Miller et al. ..................... 548/262 |
| 4,507,140 | 3/1985 | Sugavanam ..................... 548/262 |

FOREIGN PATENT DOCUMENTS

| 031911 | 7/1981 | European Pat. Off. ............ 548/262 |
| 032200 | 7/1981 | European Pat. Off. ............ 548/262 |
| 103798 | 3/1984 | European Pat. Off. ............ 548/262 |
| 126430 | 11/1984 | European Pat. Off. ............ 548/262 |
| 143384 | 6/1985 | European Pat. Off. ............ 548/262 |

Primary Examiner—Glennon H. Hollrah
Assistant Examiner—Patricia L. Morris
Attorney, Agent, or Firm—Cushman, Darby & Cushman

[57] ABSTRACT

Triazole compounds useful as plant growth regulators of the formula

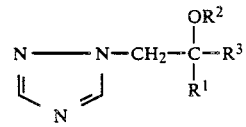

and stereoisomers thereof, wherein $R^1$ is selected from alkyl and haloalkyl groups, $R^2$ is hydrogen, and $R^3$ is a tertiary butyl group optionally substituted by halogen; and acid addition salts, and metal complexes thereof.

5 Claims, No Drawings

TRIAZOLYLMETHYL TERT-BUTYL CARBINOL DERIVATIVES WHICH HAVE PLANT GROWTH REGULATING PROPERTIES

This is a continuation application of Ser. No. 892,363, filed Aug. 4, 1986, now abandoned.

This invention relates to heterocyclic compounds useful as plant growth regulating agents, to processes for preparing them, to compositions containing them and to methods of regulating plant growth using them.

In European Patent Publication No. 0052424A there are described certain triazole and imidazole compounds in respect of which details of fungicidal activity are disclosed. The compounds are also stated to be useful for their plant growth regulating effects, although no experimental details are provided. We have now found that certain selected triazole compounds falling within the broad scope of the disclosure of EP 0052424 have unexpectedly and surprisingly superior plant growth regulating properties.

According to the present invention there is provided a triazole derivative having the general formula (I)

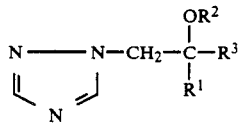

and stereoisomers thereof, wherein $R^1$ is an alkyl group containing from 4 to 9 carbon atoms, or a haloalkyl group containing from 3 to 8 carbon atoms, or a group $-CH_2-CH_2-Z$ wherein Z is an optionally substituted cycloalkyl or cycloalkenyl group containing from 3 to 8 carbon atoms in the cycloalkyl or cycloalkenyl ring; $R^2$ is hydrogen or an alkyl group containing from 1 to 4 carbon atoms; and $R^3$ is a tertiary butyl group optionally substituted by halogen; and salts, esters and metal complexes of the compound of formula (I) wherein $R^2$ is hydrogen.

The compounds of the invention may contain chiral centres. Such compounds are generally obtained in the form of racemic mixtures. However, these and other mixtures can be separated into the individual isomers by methods known in the art, and this invention embraces such isomers.

Preferred groups $R^2$ are hydrogen or methyl. Hydrogen is especially preferred.

$R^1$ may be a branched or straight chain alkyl group or haloalkyl group and is preferably a branched or straight chain alkyl group containing from 4 to 7 carbon atoms or a branched or straight chain haloalkyl group containing from 3 to 6 carbon atoms. When $R^1$ is a haloalkyl group, it preferably contains a single halogen atom. Preferred halogen atoms are chlorine, bromine and fluorine, and especially chlorine.

As examples of the group Z when $R_1$ is $-CH_2CH_2-Z$, there may be mentioned for example cyclopropyl, cyclobutyl, cyclopentyl, cyclohexyl, cyclopentenyl and cyclohexenyl. The group Z may be substituted for example by lower alkyl groups (for example alkyl groups containing from 1 to 4 carbon atoms) or halogen, but is preferably unsubstituted.

$R^3$ is preferably a tertiary butyl group, optionally substituted by a single halogen atom. Preferred halogen atoms are fluorine, chlorine and bromine, and especially fluorine and chlorine.

The present invention includes salts, esters and metal complexes of the compounds of formula (I) wherein $R^2$ is hydrogen. As examples of esters there may be mentioned for example acetates or benzoates. As examples of salts, there may be mentioned toluene sulphonate salts, dodecyl benzene sulphonate salts, hydrochloride salts, hydrobromide salts and orthophosphate salts. Without limitation of the generality of the above statement, the present invention also includes any compound which breaks down in agrochemical use to form a compound of formula (I).

Examples of the compounds of the invention are shown in Table I below in which the different values for $R^1$ and $R^2$ in the general formula (I) above are presented and $R^3$ has the structure:

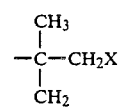

where X is as indicated in Table I.

TABLE I

| COMPOUND NO. | $R_1$ | $R_2$ | X | M.pt. (°C.) | COMMENTS |
|---|---|---|---|---|---|
| 1 | $-CH_2CH_2CH_2CH_3$ | H | H | oil | |
| 2 | $-CH_2CH_2CH_2CH_2CH_3$ | H | H | 74.5–77.5 | |
| 3 | $-CH_2CH_2CH_2CH_2CH_3$ | $CH_3$ | H | oil | |
| 4 | $-CH_2CH_2CH_2CH_2CH_2CH_3$ | H | H | oil | |
| 5 | $-CH_2CH_2CH_2CH_2CH_2CH_2CH_3$ | H | H | oil | |
| 6 | $-CH_2CH_2CH(CH_3)_2$ | H | H | 59–61.5 | |
| 7 | $-CH_2CH_2CH(CH_3)CH_2CH_3$ | H | H | oil | |
| 8 | $-CH_2CH_2CH_2CH(CH_3)_2$ | H | H | 45–48 | |
| 9 | $-CH_2CH_2CH_2CH_2CH(CH_3)_2$ | H | H | oil | |
| 10 | $-CH_2CH_2CH(CH_3)CH_2CH_2CH_3$ | H | H | oil | 1:1 mixture of isomers |
| 11 | $-CH_2CH_2CH_2CH(CH_3)CH_2CH_3$ | H | H | oil | |
| 12 | $-CH_2CH_2-C(CH_3)_3$ | H | H | 76–78 | |
| 13 | $-CH_2CH_2CH_2CH_2CH_2Cl$ | H | H | oil | |
| 14 | $-CH_2CH(CH_3)CH_2CH_2CH_3$ | H | H | oil | |
| 15 | $-CH_2CH(CH_2CH_3)_2$ | H | H | oil | |
| 16 | $-CH(CH_3)CH_2CH_2CH_2CH_3$ | H | H | oil | mixture of isomers |
| 17 | $-CH_2CH_2CH_2CH_2Cl$ | H | H | gum | |
| 18 | $-CH_2CH_2CH_2CHClCH_3$ | H | H | 47.5–51 | mixture of diastereoisomers |
| 19 | $-CH_2CH_2CH_2CH_2CH_3$ | H | F | gum | |
| 20 | $-CH_2CH_2CH_2CH_2CH_2CH_3$ | H | F | oil | |

TABLE I-continued

| COMPOUND NO. | R$_1$ | R$_2$ | X | M.pt. (°C.) | COMMENTS |
|---|---|---|---|---|---|
| 21 | —CH$_2$CH$_2$CH$_2$CH$_2$CH$_3$ | H | Cl | gum | |
| 22 | —CH$_2$CH$_2$-cyclohexyl | H | H | 63–67 | |
| 23 | —CH$_2$CH$_2$-cyclopentyl | H | H | 75.5–77 | |
| 24 | —CH$_2$CH$_2$-cyclopropyl | H | H | 57–59 | |
| 25 | —CH$_2$CH$_2$-cyclobutyl | H | H | 64–66 | |

Examples of salts of Compound No. 2 of Table I are shown in Table II below in which the acid for which the salt is derived is indicated in column 1.

TABLE II

| | Acid | Melting point of salt with Compound No. 2 (°C.) |
|---|---|---|
| 2A. | CH$_3$—C$_6$H$_4$—SO$_3$H | Low melting solid |
| 2B. | C$_{12}$H$_{25}$—C$_6$H$_4$—SO$_3$H | oil |
| 2C. | HCl | 144–151 |
| 2D. | HBr | hygroscopic solid |
| 2E. | H$_3$PO$_4$ | Low melting solid |

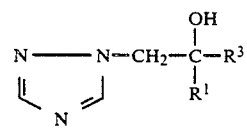

(II)

Compounds of general formula (II) may be prepared by reacting a compound of general formula (IIIa) or (IIIb)

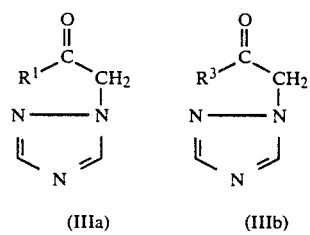

(IIIa)    (IIIb)

wherein R$^1$ and R$^3$ are as defined above, with an organometalic compound which may be represented by the general formula (IVa) or (IVb) respectively.

R$^3$M    (IVa)        R$^1$M    (IVb)

wherein R$^1$ and R$^3$ are as defined above and M is a metal which is preferably lithium, magnesium, titanium or zirconium. The reaction conveniently takes place in a solvent such as diethyl ether, tetrahydrofuran or dichloromethane at −80° C. to +80° C. in an inert atmosphere. The product is worked up by quenching with a proton donor. When M is magnesium the organometallic compound is more specifically R$^1$Mg halogen or tBu halogen. When M is titanium the organometallic compound is more specifically R$^1$Ti(O-alkyl)$_3$ or tBuTi(O-alkyl)$_3$. When M is zirconium the organometallic compound is more specifically R$^1$Zr(O-alkyl)$_3$ or tBuZr(O-alkyl)$_3$.

The compound of general formula (I) may also be prepared by reacting a compound of general formula (V) or (VI):

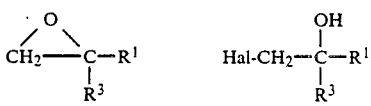

(V)    (VI)

in which R$^1$ and R$^3$ are as defined above and Hal is a halogen atom (preferably a chlorine or bromine atom), with 1,2,4-triazole either in the presence of an acid-binding agent (for example potassium carbonate) or in the form of one of its alkali metal salts in a convenient solvent.

We have found that reaction of the compound of general formula (V) or (VI) with 1,2,4-triazole in the presence of an acid binding compound such as potassium carbonate in a solvent such as dimethylformamide may give a mixture in which the 1-substituted triazole predominates and in which the 4-substituted triazole is present as a minor component. The mixture may be used without isolating the position isomers, but if desired, the isomers may be readily separated, for example by fractional crystallisation or vacuum distillation. We have found conversely that reaction of the compound of general formula (V) or (VI) with an alkali metal salt of 1,2,4-triazole generally produces essentially the 1-substituted triazole.

Thus if it is desired to produce only the 1-substituted triazole the compound of general formula (IV) or (V) may be reacted at 20°-120° C. with the sodium salt of 1,2,4-triazole. The salt can typically be prepared by adding either sodium hydride or sodium methoxide to 1,2,4-triazole in a convenient solvent such as acetonitrile, methanol, ethanol or dimethylformamide. The product can be isolated by pouring the reaction mixture into water and extracting the product with a suitable organic solvent for example diethyl ether, ethyl acetate or dichloromethane.

The ethers (wherein $R^2$ is alkyl) and the esters of the invention are made from the hydroxy compounds by reacting them with the appropriate halide, acid chloride or acid anhydride in the presence of a suitable base.

The compounds of general formula (V) can be prepared by reacting the appropriate compound of general formula (VII):

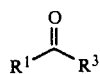

(VII)

wherein $R^1$ and $R^3$ are as defined above, with dimethylsulphonium methylide (JACS 1962, 84, 3782) or dimethylsulphoxonium methylide (JACS 1965, 87, 1353) using methods set out in the literature.

The ketones of general formula (VII) may be prepared using standard methods set out in the literature.

Ketones of general formula (VII) which are difficult to prepare by conventional means, for example wherein $R^1$ is the group —CH$_2$CH$_2$—Z and $R^3$ is unsubstituted tertiary butyl, may be prepared by hydrolysis of the corresponding diketone of formula (VIIa):

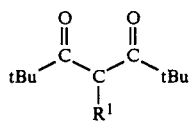

(VIIa)

wherein tBu represents the tertiary butyl group. For example the compound of formula (VIIa) may be converted into the corresponding compound of formula (VII) by treatment with a base such as sodium hydroxide in a convenient solvent such as ethanol or methanol at a temperature of 0°-100° C. The product may be worked up by Pouring the reaction mixture with water and extracted with a suitable solvent.

The compound of formula (VIIa) may be prepared by the reaction of 2,2,6,6-tetramethylheptane-3,5-dione with $R^1$Hal or $R^1$ sulphonate in the presence of an acid binding agent such as potassium carbonate in a solvent such as ethanol, methanol or dimethylformamide at 20°-100° C.

Compounds of the general formula (V) and (VI) may also be prepared by reacting a compound of general formula (VIIIa) or (VIIIb):

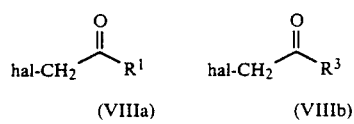

wherein $R^1$, $R^3$ and hal are as defined above, with organometallic compound of general formula (IVa) or (IVb).

The compounds of general formula (VIII) may be made using standard methods set out in the literature.

Compound of the general formula (II) may also be prepared by reacting the triazolyl epoxide (IX)

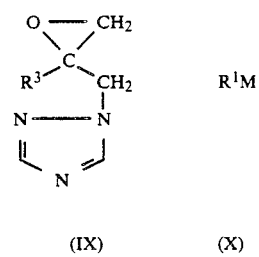

with an organometallic compound which may be represented by the general formula (X) in which $R^1$ has the meaning given previously and M is a metal which is preferably copper. The reaction conveniently takes place in a solvent such as diethyl ether or tetrahydrofuran at −80° C. to +20° C. in an inert atmosphere. The product is worked up by quenching with a proton donor. The organometallic compound may conveniently be prepared by reacting the corresponding magnesium or lithium organometallic compound with a copper (I) salt such as CuI or CuBr.SMe$_2$ complex at −80 ° to 0° C.

Compound (XI) is known in the literature (see for example DE 3111238).

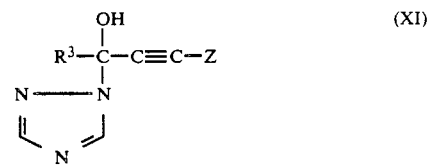

The alkyl azolyl alcohols of formula (II) where $R^1$ is the grouping —CH$_2$—CH$_2$—Z can also be made by reduction of the corresponding acetylenic alcohol (XI) using hydrogen in the presence of a suitable catalyst such as palladium on carbon (or other supports) in a suitable solvent such as methanol, ethanol or acetic acid. Reduction of such acetylenes as (XI) when the side chain, $R^1$, contains a halogen such as chlorine, can in some cases lead to hydrogenolytic removal of the halogen. In this event, the coresponding hydroxy substituted actylenic compound may be reduced and the hydroxyl group converted into a halogen group by conventional means.

The plant growth regulating effects of the compounds are manifested as, for example, by a stunting or dwarfing effect on the vegetative growth of woody and herbaceous mono- and di-cotyledonous plants. Such stunting or dwarfing may be useful, for example, in peanuts, cereals such as wheat and barley, oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agros tenuis, Cynodon dactylon* (Bermuda grass), *Dactylis glomerata*, Festuca spp. (e.g. *Festuca rubra*) and Poa spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in, for example, grasses. The compounds can also stunt weed species present in the grasses; examples of such weed species are sedges (e.g. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful, for example, for improving the quality of a sward by preferential suppression of the growth of undesirable species.

The dwarfing may also be useful in miniaturising ornamental, household, garden and nursery plants (e.g. poinsettias, chrysanthemums, carnations, tulips and daffodils).

As indicated above, the compounds can also be used to stunt woody species. This property can be used to control hedgerows or to shape or reduce the need for pruning, of fruit trees (e.g. apples, pears, cherries, peaches, vines etc).

The plant growth regulating effect may (as implied above) manifest itself in an increase in crop yield; or in an ability in orchards and other crops to increase fruit set, pod set and grain set.

Some coniferous trees are not significantly stunted by the compounds so the compounds could be useful in controlling undesirable vegetation in conifer nurseries.

In the potato, vine control in the field and inhibition of sprouting in the store may be possible.

In addition the compounds may be useful as abscision agents resulting in thinning of fruit on the tree and an increase in fruit quality.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, e.g. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (e.g. rice), the number of flowering shoots per unit area may be increased thereby increasing the overall grain yield of such crops. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, e.g. as granules or a granular formulation, for example as slow release granules, to nursery boxes, paddy water and other like cultivation loci and media. In grass swards, especially amenity grass, an increase in tillering could lead to a denser sward which may result in increased resilience in wear; and to increased yields and better quality of forage grass, e.g. improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (i.e. the harvested yield as a proportion of the total dry matter produced) by altering dry matter partitioning. This applies to all the aforementioned root, pod, cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

It is to be understood that not all the compounds of the present invention will necessarily show all the above mentioned plant growth regulating effects. Thus whilst there may be advantages in compounds which have a broad spectrum of plant growth regulating effects against a wide range of species, compounds having a high specific activity with respect to a particular species and/or plant growth regulating effect may also be of great benefit.

The Examples show that the compounds of the present invention are generally very effective as retardants on temperate cereals such as wheat and barley and on rice and apples. The compounds generally show excellent reduction of interligular length, which is an indication of internode reduction in mature plants and consequent limitation of the susceptibility of the plants to lodging. The compounds of the present invention are also generally active as retardants on woody species such as apples and vines, providing scope for their use as field management aids. The compounds generally have a substantial green-up effect associated with the activity, and in cereals can influence the tillering which may lead to increased ear number at maturity and hence increases in yield.

Certain of the compounds of the present invention show a more specific mode of action. Thus for example compound no 5 in Example 27, although relatively less active on barley and rice is very active on apples, showing substantial activity even at lower rates of application.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for plant growth regulating purposes but are more conveniently formulated into compositions for such usage. The invention thus provides a plant growth regulating composition comprising a compound of general formula (I) as hereinbefore defined, or a salt or metal complex thereof; and, optionally, a carrier or diluent.

The invention also provides a method of regulating plant growth, which comprises applying to the plant, to seed of a plant or to the locus of a plant or seed, a compound, or a salt or metal complex thereof, as hereinbefore defined, or a composition combining the same.

The compounds, salts, metal complexes, ethers and esters can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatement. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a micro-encapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% to 10%, or 0.01% to 10%, by weight of active ingredient(s) may be used.

The compositions of this invention can comprise also one or more additional compound(s) having biological activity, e.g. compounds having similar or complementary fungicidal or plant growth activity or compounds having plant growth regulating, herbicidal or insecticidal activity.

The additional fungicidal compound can be, for example, one which is capable of combating ear diseases of cereals (e.g. wheat) such as *Septoria, Gibberella* and *Helminthosporium* spp., seed and soil borne diseases and downy and powdery mildews on grapes and powdery mildew and scab on apple etc. Examples of suitable additional fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazatine, dodine fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenaponil, ofurace, propiconazole, etaconazole and fenpropemorph and fenpropidine.

The compounds of general formula (I) can be mixed with soil, peat or other rooting media for the protection of plants against seed-borne, soil-borne or foliar fungal diseases.

Suitable additional insecticides are Pirimor, Croneton, dimethoate, Metasystox, pyrethroid insecticides and formothion.

The other, additional, plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will also be herbicides.

Examples of suitable plant growth regulating compounds, which can display synergy in admixture, or use, with the invention compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluorecol), maleic hydrazide, glyphosate, glyphosine, long chain fatty alcohols and acids, dikegulac, fluoridamid, mefluidide, substituted quaternary ammonium and phosphonium compounds (e.g. chlormequat* chlorphonium or mepiquat chloride*), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat*, benzoylprop-ethyl 3,6-dichloropicolinic acid, fenpentezol, triapenthanol, flurpirimidol, paclobutrazol, tetcyclacis and tecnazene. Synergy will be most likely to occur with those of the foregoing which are quaternary ammonium compounds and with those marked with an asterisk.

For certain applications, for example in the injection to the compounds of the invention into trees or plants, it is desirable that the compounds have a relatively high solubility in water, for example a solubility in excess of 30 parts per million. The compounds may be used as an aqueous solution only or may be formulated for injection, for example as a solution in a lower alcohol.

For certain applications it is also desirable that the compound has a low persistancy in soil to prevent carry-over to adjacent crops or even crops planted subsequently in the same soil. Preferably the compound for use in such applications has a half life in the soil of less than 20 weeks.

The invention is illustrated by the following Examples.

EXAMPLE 1

This Example illustrates the preparation of Compound No. 1 of Table I (2,2-dimethyl-3-hydroxy-3(n-butyl)-4-(1,2,4-triazol-1-yl)-butane).

To a mixture of n-butyl lithium (23 ml of a 1.55M solution in hexane) in dry diethyl ether (50 ml), at −10° C. under nitrogen, was added chlorozirconium-tri-n-butoxide (20 ml of a 2.0M solution in diethyl ether). The mixture was stirred at 0° C. for 1 hour, then a solution of 2,2-dimethyl-4-(1,2,4-triazol-1-yl)-butane-3-one (2.0g, 12 mmol) in dry dichloromethane (25 ml) was added. The reaction mixture was warmed to room temperature and stirred overnight. The reaction mixture was poured into dilute hydrochloric acid (0.5M) and the aqueous portion extracted with ethyl acetate. The combined ethyl acetate extracts were washed with water, saturated sodium bicarbonate solution and brine, dried (anhydrous MgSO₄), and concentrated in vacuo to give a yellow oil. Chromatography on silica using gradient elution (ethyl acetate 20–80% in petrol) gave the product (0.48 g) as a yellow oil.

NMR (CDCl₃)δ0.50–1.60 (18H,cmplx), 2.92 (1H,s), 4.30 (2H,s), 7.94 (1H,s), 8.16 (1H,s).

IR (film) 3160–3700 (strong), 3520 cm⁻¹.

m/e no M⁺, 210, 168, 143, 82.

EXAMPLE 2

This Example illustrates the preparation, in two stages, of the triazolyl alcohol having the formula

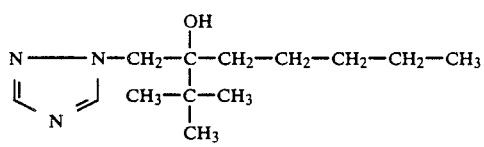

Compound 2 of Table I (2,2-dimethyl-3-hydroxy-3-(n-pentyl)-4-(1,2,4-triazol-1-yl)-butane).

Stage 1

The preparation of the epoxide of structure

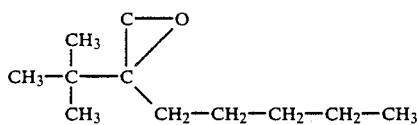

A suspension of sodium hydride (50%) (5.47 g, 0.115M) prewashed with petroleum ether (40°-60°) in dry dimethyl sulphoxide (80 mls) was heated at 60° for 2 hours. The mixture was cooled to room temperature, dry tetrahydrofuran (80 mls) added and then further cooled to 0° C. Trimethylsulphonium iodide (23.53 g, 0.115M) in dry dimethyl sulphoxide (70 mls) was added dropwise keeping the temperature of the mixture at 3° C. or below. After complete addition of the trimethylsulphonium iodide solution the mixture was stirred for one more minute and then a solution of 2,2-dimethyloctan-3-one (12.0 g, 0.07M) in dry tetrahydrofuran (20 mls) was added rapidly. After stirring at 0° C. for 1 hour the cooling bath was removed and the reaction mixture was stirred for 16 hours. The reaction mixture was then poured into water and extracted with ether. The combined ethereal extracts were washed with brine, dried (anhydrous MgSO₄) and the ether removed in vacuo to give the epoxide as a yellow oil which was used without further purification.

Stage II

The preparation of the triazolyl alcohol

To a suspension of sodium hydride (50%) (2.16 g, 0.045M) in dry dimethylformamide (50 mls) was added, portionwise, 1,2,4-triazole (3.0 g, 0.045M). The reaction mixture was stirred at room temperature for 20 minutes and then the epoxide, prepared as described in Stage I, was added dropwise. The resultant mixture was heated at 80° C. for 4 hours then at 110° C. for 3 hours. The reaction mixture was then cooled and the dimethylformamide removed in vacuo. The residue was partitioned between water and ether. The ether layer was removed and the aqueous further extracted with ether. The combined ethereal extracts were washed with brine, dried (anhydrous MgSO₄) and evaporated. The residue was chromatographed on silica using gradient elution (ethyl acetate (0–100%) in petrol) to give the triazolyl alcohol (5.2 g) as a pale orange oil. The oil crystallised on standing to give a cream solid. Trituration with petrol (40–60) gave a white solid (melting point 74.5°–77.5° C.).

NMR (CDCl₃)δ1.0 (9H,s), 0.6–1.7(11H,cmplx), 2.9 (1H, broad s), 4.30 (2H, s), 7.95 (1H,s), 8.18 (1H,s).

IR (liquid film) 2500–3700 (strong) cm⁻¹.

m/e no M⁺, 224, 182, 168, 157, 83, 70.

EXAMPLE 3

This Example illustrates the preparation of the methyl ether of the triazolyl alcohol of Example 2, and having the formula:

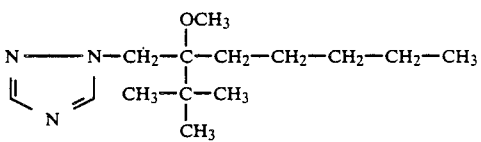

Compound 3 of Table I

To a solution of the triazolyl alcohol prepared as in Example 2 (1.20 g, 0.005M) in dry dimethylformamide (10 mls) was added, portionwise, sodium hydride (50%) (0.24 g, 0.005M). The reaction mixture was stirred at room temperature for 20 minutes then methyl iodide (0.71 g, 0.005M) was added dropwise. The resulting mixture was heated at 80° C. for 5 hours then cooled and the dimethylformamide removed in vacuo. The residue was partitioned between water and ether. The ether layer was removed and the aqueous was further extracted with ether. The combined ethereal extracts were washed with brine, dried (anhydrous MgSO₄) and evaporated. The residue was chromatographed on silica using gradient elution (ether (0–100%) in petrol) to give the O-methyl ether (0.48 g) as a pale yellow oil.

NMR (CDCl₃)δ0.88 (3H,t), 1.00 (9H,s), 1.1–1.6 (8H,cmplx), 3.30 (3H,s), 5.30 (2H,AB quartet), 7.86 (1H,s), 8.17 (1H,s).

IR (liquid film) 2800–3050 (strong) 3130 (weak) cm⁻¹.

m/e no M⁺, 238, 222, 196, 182, 171.

EXAMPLE 4

This Example illustrates the preparation, in two stages, of the triazolyl alcohol having the formula

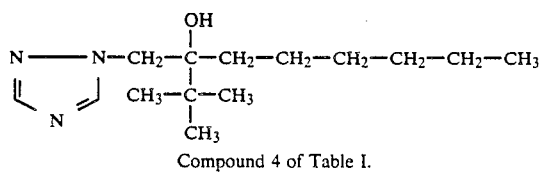

Compound 4 of Table I.

(2,2-dimethyl-3-hydroxy-3(n-hexyl)-4-(1,2,4-triazol-1-yl)butane).

Stage 1

The preparation of the epoxide of structure

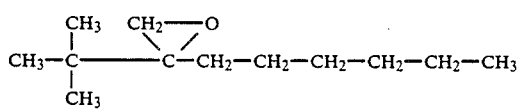

A suspension of sodium hydride (50%) (3.75 g, 0.078M) prewashed with petroleum ether (40°-60°) in dry dimethyl sulphoxide (120 mls) was heated at 60° C. for 2 hours. The mixture was cooled to room temperature, dry tetrahydrofuran (80 mls) added and then further cooled to 0° C. Trimethylsulphonium iodide (15.9 g, 0.078M) dissolved in dry dimethyl sulphoxide (80 mls) was added dropwise keeping the temperature of the mixture at 3° C. or below. After complete addition of the trimethylsulphonium iodide solution the mixture was stirred for one more minute and then a solution of 2,2-dimethylnonan-3-one (6.65 g, 0.039M) in dry tetrahydrofuran (20 mls) was added rapidly. After stirring at 0° C. for 1 hour the cooling bath was removed and the reaction mixture was stirred for 16 hours. The reaction mixture was poured into water and extracted with ether. The combined ethereal extracts were washed with brine, dried (anhydrous MgSO$_4$) and the ether removed in vacuo to give the epoxide as a yellow oil which was used without further purification.

Stage II

The preparation of the triazolyl alcohol

To a suspension of sodium hydride (50%) (3.75 g, 0.078M) in dry dimethylformamide (200 mls) was added, portionwise, 1,2,4-triazole (5.46 g, 0.078M). The reaction mixture was stirred at room temperature for 20 minutes then the epoxide prepared as described in Stage I was added dropwise. The resultant mixture was heated at 80° C. for 6 hours, cooled and then poured into water and extracted with ether. The combined ethereal extracts were washed with brine, dried (anhydrous MgSO$_4$) and evaporated. The residue was chromatographed on silica using gradient elution (ethyl acetate (0-100%) in petrol) to give the triazolyl alcohol (4.68 g) as a yellow oil.

NMR (CDCl$_3$)δ1.00 (9H,s), 0.8-1.7 (13H,cmplx) 2.82(1H,s) 4.29 (2H,s), 7.94 (1H,s), 8.15 (1H,s).

IR (liquid film) 2800-3700 (strong) cm$^{-1}$.

m/e no M$^+$, 196, 171, 168, 83, 70.

EXAMPLE 5

This Examples illustrates the preparation of Compound No 5 of Table I (2,2-dimethyl-3-hydroxy-3-(n-heptyl)-4-(1,2,4-triazol-1-yl)-butane).

Stage I

Preparation of 2,2-dimethyl-3-hydroxy-3-(hept-1-yne-1-yl)-4-(1,2,4-triazol-1-yl)-butane.

To a solution of hept-1-yne (3.9 g, 0.041 mol) in dry tetrahydrofuran (30 mls) at −70° C. under nitrogen was added n-butyl lithium (30 mls of a 1.55M solution in hexane) and the resulting mixture stirred for 1 hour. To this mixture was added a solution of 2,2-dimethyl-4-(1,2,-4-triazol-1-yl)-butane-3-one (6.8 g, 0.041 mol) in dry tetrahydrofuran (50 mls), and the resulting mixture was allowed to warm to room temperature. The reaction mixture was partitioned between ethyl acetate and aqueous HCl (1.0M). The aqueous was further extracted with ethyl acetate. The combined ethyl acetate extracts were washed with water, saturated sodium bicarbonate solution and brine, dried (anhydrous MgSO$_4$) and then concentrated in-vacuo to give a yellow oil. Chromatography on silica using gradient elution (diethyl ether 20-80% in petrol) gave the title compound (2.87 g) as a yellow crystalline solid melting point 76°-78° C.).

NMR (CDCl$_3$)δ0.70-1.00 (3H, tJ7Hz), 1.10-1.50 (15H, cmplx) 1.80-2.10 (2H, cmplx), 3.75 (1H, s), 4.30 (2H, s), 7.95 (1H, s), 8.18 (1H, s).

IR (nujol) 3080-3600 (strong), 3130, 2250 cm$^{-1}$.

m/e no. M$^+$, 248, 206, 181, 82.

Analysis C$_{15}$H$_{25}$N$_3$O requires: C, 68.40; H, 9.57, N, 1.95%. found: C, 68.38; H, 9.43, N, 1.90%.

Stage II

To a solution of the alcohol prepared in Stage I (1 g, 0.038 mol) in ethyl acetate (50 ml) was added a catalyst containing 10% palladium on carbon (0.5 g), and the resulting solution was hydrogenated at 60 psi H$_2$ for 30 hours. The reaction mixture was then filtered through wet 'Hyflo'. The organic layer was washed with water and brine, dried (anhydrous MgSO$_4$) and concentrated in vacuo to give the crude product.

Chromatography on silica using gradient elution (diethyl ether 20-80% in petrol) gave the title compound (0.66 g) as an oil.

NMR (CDCl$_3$)δ0.60-1.60 (24H, cmplx), 2.86 (1H,s), 4.30 (2H,s), 7.92 (1H,s), 8.16 (1H,s).

IR (film) 3175-3600, 3125 (weak).

m/e 266, 252, 210, 185, 168, 82.

EXAMPLE 6

This Examples illustrates the preparation in three stages of Compound No 6 of Table I (2,2-dimethyl-3-hydroxy-3-(4-methyl-but-1-yl)-4-(1,2,4-triazol-1yl)-butane).

Stage I

Preparation of 2,2,6-trimethylheptan-3-one

To a stirred mixture of pivaloyl chloride (6.02 g, 0.05 m) and copper (I) iodide (0.10 g, 0.6 mm) in dry ether (50 mls) at −60° C. under nitrogen was added dropwise isoamyl magnesium bromide [prepared from magnesium turnings (1.8 g, 0.075 m) and isoamyl bromide (7.55 g, 0.05 m) in dry ether (70 mls]. The cooling bath was removed and the reaction mixture stirred for 16 hours then poured cautiously into ice-cold dilute hydrochloric acid and extracted with ether. The combined ethereal extracts were washed with saturated aqueous sodium hydrogen carbonate solution, brine, dried (anhydrous MgSO₄) and evaporated. The residue was chromatographed on silica using gradient elution (dichloromethane (0-30%) in petrol) to give the ketone as a pale yellow oil.

Stage II

The preparation of the epoxide of structure III

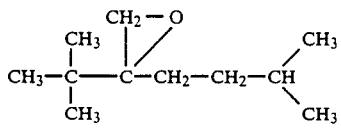

A suspension of sodium hydride (50%) (2.4 g, 0.05 m), prewashed with petroleum ether (40°-60°) in dry dimethyl sulphoxide (100 mls) was heated at 60° C. for 2 hours. The mixture was cooled to room temperature, dry tetrahydrofuran (80 mls) added and then further cooled to 0° C. Trimethylsulphonium iodide (10.2 g, 0.05 m) dissolved in dry dimethyl sulphoxide (80 mls) was added dropwise keeping the temperature of the mixture at 3° C. After complete addition of the trimethylsulphonium iodide solution the mixture was stirred for one more minute and then a solution of the ketone prepared as described in Stage I in dry tetrahydrofuran (20 mls) was added rapidly. After stirring at 0° C. for 1 hour the cooling bath was removed and the reaction mixture was stirred for 16 hours. The reaction mixture was poured into water and extracted with ether. The combined ethereal extracts were washed with brine, dried (anhydrous MgSO₄) and the ether removed in vacuo to give the epoxide as a pale yellow oil which was used without further purification.

Stage III

Preparation of the triazolylalcohol (Compound No 6)

To a suspension of sodium hydride (50%) (1.44 g, 0.03 m) in dry dimethylformamide (20 mls) was added portionwise, 1,2,4-triazole (2.07 g, 0.03 m). The reaction mixture was stirred at room temperature for 20 minutes then the epoxide prepared as described in Stage II was added dropwise. The resultant mixture was heated at 80° C. for 6 hours cooled then poured into water and extracted with ether. The combined ethereal extracts were washed with brine, dried (anhydrous MgSO₄) and evaporated. The residue was chromatographed on silica using gradient elution (ethyl acetate 10-100% in petrol) to give the triazolyl alcohol Compound No 6 (1.78 g) (m.pt. 59°-61.5° C.) as a white solid.

NMR (CDCl₃)δ0.73 (3H, d J7Hz), 0.80 (3H, d J7Hz), 1.01 (9H,s), 1.0-1.8 (5H, cmplx), 2.85 (1H,s), 4.30 (2H,s), 7.95 (1H,s), 8.15 (1H,s).
IR (niyol) 3050-3650 (strong) cm⁻¹.
m/e 240, 222, 182, 83, 70.

EXAMPLE 7

This Example illustrates the preparation of Compound No 7 of Table I (2,2-dimethyl-3-hydroxy-3-(3-methyl-pent-1-yl)-4-(1,2,4-triazol-1-yl)-butane).

Stage I

10 To a solution of ethyl magnesium bromide (20 ml) of a 3M solution in diethyl ether) in dry diethyl ether (30 ml) under N₂ at room temperature was added a solution of 3-methyl-1-pentyne (5 g, 0.06 mol) in diethyl ether (20 ml). The resulting mixture was heated under reflux for 1 hour, and then cooled to 0° C. To this mixture was added slowly a solution of 2,2-dimethyl-4-(1,2,4-triazol-1-yl)-butane-3-one (8.4 g, 0.05 mol) in dry dichloromethane (150 ml), and the mixture stirred for 45 minutes, a gelatinous precipitate formed. Ammonium chloride solution was added to the mixture, and the organic layer separated and washed with water and brine, dried over MgSO₄ and concentrated in vacuo. The residue was chromatographed on silica eluting with diethyl ether (20-100%) in petrol gave 2,2-dimethyl-3-hydroxy-3-(3-methyl-pent-1-yne-1-yl)-4-(1,2,4-triazol-1-yl)-butane) as a white solid (4.29 g) (mpt=59°-60° C.).

Stage II

To a solution of the alcOhol perpared in Stage I (0.78 g, 3-1 mmol) in ethanol (20 ml) was added a catalyst containing 10% palladium on carbon (0.5 g), and the resulting mixture was hydrogenated at 60 psi H₂ for 5 days. The reaction mixture was filtered through "Hyflo", washing through with ethyl acetate. The solution was evaporated to dryness and column chromatography of the crude product on silica using gradient elution (diethyl ether 20-80% in petrol) gave Compound No 7 (0.74 g) as an oil.

The product was characterised by the following data:
NMR (CDCl₃)δ1.01 (9H,s), 0.68-1.76 (13H, cmplx), 2.89 (1H, cmplx); 4.30 (2H,s), 7.98 (1H,s), 8.16 (1H,s).
IR (film) 3160-3700 (strong), 3120 cm⁻¹.
m/e 254 (MH+), 238, 196, 171, 168, 82, 57.
Analysis C₁₄H₂₇N₃O, requires: C, 66.36; H, 10.74; N, 16.58%. found: C, 66.09; H, 11.27; N, 16.17%.

EXAMPLE 8

Compound No 8 of Table I (2,2-dimethyl-3-hydroxy-3-(4-methyl-pent-1-yl)-4-(1,2,4-triazole-1-yl)-butane) was prepared by hydrogenation of the corresponding alkyne using the general method of Example 7. The product was a white solid having a melting point of 45°-48° C. and characterised by the following data:
NMR (CDCl₃)δ0.66 (6H, d), 1.00 (9H, s), 0.44-1.68 (7H, cmplx), 2.82 (1H, s), 3.18 (2H, s), 7.96 (1H, s), 8.16 (1H, s).
IR (film) 3145-3700 (strong), 3120 cm⁻¹.
m/e 254 (MH+), 238, 220, 196, 168, 83, 57.
Analysis C₁₄H₂₇N₃O, requires C, 66.36; H, 10.74; N, 16.58%. found: C, 65.90; H, 10.63; N, 16.63%.

EXAMPLE 9

Compound No 9 of Table I (2,2-dimethyl-3-hydroxy-3-(5-methyl-hex-1-yl)-4-(1,2,4-triazol-1-yl)-butane) was prepared by hydrogenation of the corresponding alkyne using the general method of Example 7. The product was an oil characterised by the following data:
NMR (CDCl₃)δ0.68-1.60 (24H, cmplx), 2.82 (1H, s), 4.30 (2H, s), 7.94 (1H, s), 8.15 (1H, s).
IR (film) 3150-3650 (strong), 3125 cm⁻¹.
m/e No M+, 252, 210, 185, 82, 57.

EXAMPLE 10

Compound No 10 of Table I was prepared using the general method of Example 7. The product, a 1:1 mixture of diastereoisomers, was an oil characterised by the following data:

NMR (CDCl$_3$)δ0.66–1.65 (24H, cmplx), 2.87 (1H, s), 4.30 (2H, s), 7.95 (1H, s), 8.16 (1H, s).
IR (film) 3180–3630, 3130 cm$^{-1}$.
m/e No M$^+$, 252, 210, 185, 82, 57.

EXAMPLE 11

Compound No 11 of Table 1 was prepared using the general method of Example 7. The product was a colourless oil characterised by the following data:
NMR (CDCl$_3$)δ0.50–1.70 (24H, cmplx), 2.82 (1H, s), 4.08 (2H, s), 7.94 (1H, s), 8.16 (1H, s).
IR (film) 3160–3640, 3120 cm$^{-1}$.
m/e No M$^+$, 210, 185, 82, 57.

EXAMPLE 12

Compound No 12 of Table I (2,2-dimethyl)-3-hydroxy-3-(3,3-dimethyl-but-1-yl)-4-(1,2,4-triazol-1-yl)-butane) was prepared using the general method of Example 6 but using 2,2-dimethyl-4-bromobutane as the starting material in the first stage preparation of 2,2,6,6-tetramethylheptan-3-one.

The product was a white solid having a melting point of 76°–78° C., and characterised by the following data:
NMR (CDCl$_3$)δ0.78 (9H, s), 1.04 (9H, s), 0.4–1.6 (4H, cmplx), 2.9 (1H, s), 4.32 (2H, s), 7.96 (1H, s), 8.26 (1H, s).
IR (film) 3160–3700, 3120 (weak) cm$^{-1}$.
m/e No M$^+$, 238, 196, 82.

EXAMPLE 13

This Example illustrates the preparation of Compound 22 of Table I.

Stage 1

Preparation of 2,2-dimethyl-3-cyclohexylethyl propan-3-one

Stage 1 of the preparation was carried out under an argon atmosphere. To a stirred solution of t butyl alcohol (4.92 g) in tetrahydrofuran (20 ml) at −30° C. was added dropwise n-butyl lithium (41.8 ml of 1.6 molar solution). The resultant lithium t-butoxide solution was allowed to warm to 0° C. and was added to a stirred solution of cuprous iodide (12.65 g) in tetrahydrofuran (50 ml). After about 15 minutes, the grey cuprous iodide was replaced by a beige solid, and the reaction mixture turned brown. The reaction mixture was then cooled to −70° C. and t-butyl lithium (34.0 ml of 1.9 molar solution) was added dropwise. A cooled (−40° C.) solution of 3-cyclohexyl propionic acid chloride (10 .0 g) in tetrahydrofuran (20 ml) was added rapidly. After 1½ hours, the reaction was quenched by the addition of methanol (30 ml) and the reaction mixture was allowed to stand overnight at room temperature. The mixture was then poured into saturated ammonium chloride (200 ml) and insolubles were filtered off. The aqueous layer was extracted with ether (300 ml) and the extract was washed with 1% sodium thiosulphate solution (200 ml) and then dried over magnesium sulphate in the presence of charcoal. Concentration yielded an amber oil which was distilled to give a colourless liquid (5.56 g) which turned yellow on standing.

Stage 2

Formation of 2-t-butyl-2-cyclohexylethyl oxirane

A suspension of sodium hydride (from 0.84 gms of petrol-washed 80% oil dispersion) in dimethylsulphoxide (50 mls) was stirred at 60° C. for 2 hours under a nitrogen atmosphere. The solution was cooled to 20° C., diluted with dry tetrahydrofuran (50 ml) and cooled to −5° C. A slurry of trimethylsulphonium iodide (5.11 gms) in dimethyl sulphoxide (20 mls) was added followed, after 10 minutes stirring, by a solution of the product of Stage 1 in Tetrahydrofuran (20 mls). The mixture was stirred for 4 hours at room temperature stood over the weekend at 20° C., and poured into water and extracted with petrol (30°–40° C.). The extracts were washed with brine, dried and evaporated to give 3.77 gms of yellow product. The product was used without further purification.

Stage 3

Preparation of Compound 1 of Table 1

A solution of 1,2,4-Triazole (2.11 gms) in dimethyl formamide (25 ml) was added dropwise to dimethylformamide (50 mls) containing sodium hydride (from 0.73 gms of petriol-washed 80% oil dispersion). After ½ hour stirring at 20° C. a solution of the product of Stage 2 (3.77 g) in dimethylformamide (25 mls) was added. The mixture was then heated at 45°–50° C. for a total of 7 hours, poured into water and extracted with ether. The extracts were washed with water, dried and concentrated to a white solid which was purified by thin layer chromatography to give 0.435 gms of Compound No 1 of Table I, 2,2-dimethyl-3-hydroxy-3-cyclohexylethyl-4-(1,2,4-triazol-1-yl)-butane melting point 63°–67° C.

The physical characteristics are listed below:
NMR (CDCl$_3$) 1.0 (9H,s), 0.44–1.72 (15H, complex), 2.88 (1H,s), 4.3 (2H,s), 7.96 (1H,s) 8.16 (1H,s).
IR (nujol) 3200–3640 cm$^{-1}$ (m), 3060–3180 cm$^{-1}$ (w).

EXAMPLE 14

The general procedure of Example 13 was followed using 3-cyclopentyl propionic acid chloride as starting material to give Compound No 23 of Table 1, 2-2-dimethyl-3-hydroxy-3-cyclopentylethyl-4-(1,2,4-triazol-1-yl)-butane melting point 75.5°–77° C. The product was charaterised as follows:
IR (nujol) 3140–3160 cm$^{-1}$ (w), 3160–3600 cm$^{-1}$ (m)
NMR (CDCl$_3$)δ0.56–0.76 (1H, complex), 0.76–1.08 (2H, complex), 1.0 (9H,s), 1.12–1.32 (1H, complex), 1.32–1.72 (9H, complex), 2.98 (1H,s), 4.26 (2H,s), 7.92 (1H,s) 8.16 (1H,s)

EXAMPLE 15

Preparation of 3-cyclopropylethyl-2,2-dimethyl-3-hydroxy-4-(1,2,4-triazol-1-yl)butane (Compound No. 24 of Table I).

Stage 1

Preparation of 4-cyclopropylmethyl-2,2,6,6-tetramethylheptane-3,5-dione

A mixture of 2,2,6,6-tetramethyl-heptane-3,5-dione (13.3 g), cyclopropyl methyl bromide (9.0g), potassium carbonate (10.2 g) and a trace of potassium iodide in ethanol (40 ml) was refluxed for a total of 16 hours. Most of the solvent was removed and water added to the residue. The mixture was extracted with ether, the extract washed with water and then with brine, dried and concentrated to 13.07 g of a yellow oil which was distilled using a water pump until the stillhead temperature reached 144° C. Extraction of the distillation residue with ether and concentration gave the pure diketone as a beige solid m.pt. 56°–59° C.

Stage 2

Preparation of t-butyl (2-cyclopropylethyl ketone)

The diketone from the previous stage (3.60 g) was added to a warm solution of sodium hydroxide (1.80 g) in ethanol (60 ml). The solution was refluxed for 6 hours, stood at room temperature for 2 days and poured into water. The mixture was extracted with ether and the extract washed with water, dried and carefully concentrated to give the ketone containing a little ether (total of 2.84 g). This product was used directly for the preparation of the final compound following the procedure of Example 1.

3-Cyclopropylethyl-2,2-dimethyl-3-hydroxy-4-(1,2,4-triazol-1-yl)butane

Obtained as a white solid m.pt. (57°–59° C.).

NMR (CDCl$_3$)δ: 0.12 (2H,m); 0.32 (2H,m); 0.60 (1H,m); 1.00 (9H,s); 1.10 (2H,m); 1.61 (2H,m); 1.80 (1H,s); 4.28 (2H,s); 7.95 (1H,s); 8.15 (1H,s)

EXAMPLE 16

This Example illustrates the preparation of 2,2-dimethyl-1-fluoro-3-hydroxy-3-pentyl-4-(1,2,4-triazol-1-yl)-butane, compound No. 19 of Table I.

Stage 1

Preparation of 2,2-dimethyl-1-fluoro-3-hydroxy-3-(pent-1-yne-1-yl)-4-(1,2,4-triazol-1-yl)butane To a stirred solution of pent-1-yne (1.5 g, 22 mmol) in dry tetrahydrofuran (40 ml) was added n-butyl lithium (9 ml of 2.6M, 23 mmol) at −78° C. under a nitrogen atmosphere followed by chlorotitanium tri-isopropoxide (22 ml of 1M, 20 mmol). After 15 minutes, a solution of 3,3-dimethyl-4-fluoro-1-(1,2,4-triazol-1-yl)butan-2-one (prepared as in DE 2,820,361) (4.0 g, 22 mmol) in dry tetrahydrofuran (20 ml) was added dropwise. Upon complete addition the mixture was allowed to warm to room temperature and stirred for 18 hours. The reaction mixture was then poured onto ice and extracted with ether (2×250 ml). The ethereal solution was washed with saturated brine solution then dried over anhydrous magnesium sulphate and the solvent removed. The resulting yellow oil was chromatographed (silica gel, petrol/diethyl ether elution) to give a yellow gum (2.8 g).

Stage 2

The propargylic alcohol prepared in Stage 1 (2.3 g, 9.1 mmol) was dissolved in ethanol (100 ml). To this was added 5% palladium on charcoal (1.0 g). The reaction vessel was charged with hydrogen (60 psi) and shaken at room temperature for 24 hours. Examination of the reaction by glc showed incomplete hydrogenation, the flask was then recharged with hydrogen (60 psi) and shaken for a further 24 hours at 50° C. The catalyst was then filtered off and the solvent removed. The resulting residue was then chromatographed (silica gel, petrol/diethyl ether elution) to give a colourless oil (1.4 g, 60%), (Found: C, 60.2; H,9.9; N, 16.1. C$_{13}$H$_{24}$FN$_3$O requires C, 60.7; H, 9.3; N, 16.2%) IR :−3250, 2950, 1280, 1200, 1140, 1080, 940, 760, 680 cm$^{-1}$; NMR (90 MHz; CDCl$_3$) 0.84 (3H,t, J=6 Hz), 1.01 (6H,s); 1.08–1.6 (8H,m); 3.52 (1H,s); 4.36 (2H,s); 4.4 (2H,dq, J=47 and 8 Hz); 7.92 (1H,s); 8.17 (1H,s); Mass spec. m/z 258 (M+H$^+$), 186, 182, 175, 83 (100%).

EXAMPLE 17

This Example illustrates the preparation of 2,2-dimethyl-1-chloro-3-hydroxy-3-pentyl-4-(1,2,4-triazol-1-yl)butane, compound No. 21 of Table I. The title compound was prepared using from the corresponding propargylic alcohol using the general method of Example 16. The product was a yellow gum characterised as follows:

IR. 3250, 2950, 1380, 1280, 1200, 1140, 1020, 750, 680 cm$^{-1}$

NMR (90 MHz; CDCl$_3$) 0.84 (3H,t,J=6.3 Hz); 1.1 (6H,d,J=4.5 Hz); 1.12–1.3 (6H,m); 1.3–1.6 (2H,m); 3.26 (1H,br); 3.88 (2H,s); 4.58 (2H,s); 7.98 (1H,s); 8.2 (1H,s); Mass spec. m/z 274 (M+H$^+$); 202, 191, 182, 83 (100%).

EXAMPLE 18

This Example illustrates the preparation of compound No. 17 of Table I. 2,2-Dimethyl-3-hydroxy-3-(4-chlorobutyl)-4-(1,2,4-triazol-1-yl)butane.

Stage 1

Preparation of the toluene sulphonate derivative of the corresponding acetylenic compound.

To a solution of 4-toluenesulphonyl-but-1-yne (7.4 g, 33 mmol) in dry tetrahydrofuran (30 ml), at −50° C. under nitrogen, was added n-butyl lithium (21 ml of a 1.6 molar solution in hexane) and the reaction mixture was stirred for 20 minutes. A solution of chlorotitanium triisopropoxide (33 ml of a 1.0 molar solution in hexane) was added slowly and the mixture stirred for 25 minutes. A solution of triazolyl pinacolone (5.0 g, 30 ml) in tetrahydrofuran (40 ml) was added and the mixture allowed to warm slowly to room temperature. The reaction was quenched with ammonium chloride solution, and extracted with ethyl acetate (x3). The combined organic extracts were washed with water and brine, dried over anhydrous magnesium sulphate and evaporated to dryness to give a yellow oil (11.3 g). Column chromatography of the crude product on silica gel, eluting with ethyl acetate 10–80% in petrol, afforded the toluene sulphonyl derivative as a white crystalline solid (4.3 g) (mp. 90°–92° C.).

Stage 2

To a solution of the product of stage 1 (1 g, 2.56 mmol) in ethanol (50 ml) was added a catalyst containing 5% palladium on carbon (0.1 g) and the mixture was hydrogenated at 40° C. at 60 psi H$_2$ overnight. The reaction mixture was filtered, and the filtrate was concentrated in vacuo to give a pale yellow gum. Column chromatography on silica gel, eluting with diethyl ether 50–100% in petrol then ethyl acetate 5–40% in petrol, afforded the toluene sulphonate derivative of the title compound, as a yellow gum (0.27 g).

Stage 3

A mixture of the product of Stage 2 (0.26 g, 0.66 mmol) and lithium chloride (0.1 g, 2.4 mmol) in dimethyl sulphoxide (10 ml) was heated at 100° C. (bath temperature) for 3 hours. The reaction mixture was cooled to room temperature and partitioned between ethyl acetate and water. The aqueous portion was further extracted with ethyl acetate, and the combined organic extracts were washed with saturated sodium hydrogen carbonate solution, water and brine, dried over anhydrous magnesium sulphate and evaporated to dryness to give the title compound, as a yellow oil (0.18 g).

NMR (CDCl$_3$, 270 MHz)δ0.92 (9H,s); 1.1–1.5 (4H,cmplx), 1.55 (2H,cmplx); 3.00 (1H,s); 3.32 (2H,t); 4.20 (2H,s); 7.82 (1H,s); 8.08 (1H,s);

IR (film): 3500–3050, 3125, 1510 cm$^{-1}$

EXAMPLE 19

This Example illustrates the preparation of 2,2-dimethyl-3-hydroxy-3-(2-methyl-pent-1-yl)-4-(1,2,4-triazol-1-yl)butane Compound No. 14 of Table I.

To a stirred suspension of magnesium turnings (0.65 g, 27 mmol) and one crystal of iodine in dry tetrahydrofuran (10 ml), at room temperature under nitrogen, was added dropwise a solution of 2-bromopentane (3.5 g, 23 mmol) in tetrahydrofuran (20 ml). The mixture was heated under reflux for 5 minutes then cooled to room temperature and decanted off the unreacted magnesium into a dropping funnel. This solution was added slowly to a slurry of cuprous bromidedimethyl sulphide complex (4.5 g, 22 mmol) in tetrahydrofuran (20 ml) under nitrogen at $-70°$ C. and the mixture was stirred for 15 minutes. A solution of the epoxide derived from triazolyl pinacolone, (2.0 g, 11 mmol) in tetrahydrofuran (25 ml) was added dropwise to the reaction mixture which was then allowed to warm slowly to room temperature. The reaction mixture was quenched with 20% aqueous ammonium chloride solution, then extracted with ethyl acetate. The combined organic extracts were washed with dilute ammonia solution, water and brine, dried over $MgSO_4$ and evaporated to dryness. Column chromatography of the crude product on silica gel, eluting with diethyl ether (20–80%) in petrol, afforded the title compound, as a pale yellow oil (2.2 g) as a mixture of diastereoisomers.

NMR ($CDCl_3$, 270 MHz)δ: 0.6–0.9 (7H,cmplx); 0.96, 0.98 (9H, two singlets); 1.0–1.8 (6H,cmplx); 3.05, 3.11 (1H,two singlets), 4.24 (2H,two quartets); 7.96 (1H,s); 8.16 (1H,s)

Analysis: $C_{14}H_{27}N_3O$: requires C,66.36; H, 10.74; N,16.58%. found C,66.40; H,10.88; N,16.29%.

m/e No. M+, 238, 196, 171, 168, 150, 126, 109,

EXAMPLE 20

2,2-Dimethyl-3-hydroxy-3-(2-ethyl-butyl)-4-(1,2,4-triazol-1-yl)butane (Compound No. 15 of Table I) was prepared using the general method of Example 19 and was a yellow oil characterised as follows:

NMR ($CDCl_3$), 270 MHz)δ: 0.68 (3H,t); 0.78 (3H,t); 0.81 (1H,cmplx); 0.96 (9H,s); 1.05 (2H,cmplx); 1.2 (2H cmplx); 1.4 (1H,cmplx); 1.64 (1H,dd); 3.21 (1H,s); 4.24 (2H,q); 7.86 (1H,s); 8.18 (1H,s)

IR (film): 3700–3150, 3120, 1500 cm$^{-1}$ m/e No. M+, 238, 196, 171, 168, 83, 70

EXAMPLE 21

2,2-Dimethyl-3-hydroxy-3-(1-methyl-pentyl)-4-(1,2,4-triazol-1-yl)butane (Compound No. 16 of Table I) was prepared using the general method of Example 6.

The product was a yellow oil (a mixture of diastereoisomers) which was characterised as follows.

NMR ($CDCl_3$, 270 MHz) 0.6–0.9 (6H,cmplx); 1.0, 1.04 (9H,two singlets); 1.15–1.4 (5H,cmplx); 1.5–1.8 (2H,cmplx); 3.60, 3.64 (1H,two singlets); 4.36 (2H,two quartets); 7.93 (1H,s); 8.14 (1H,s)

IR (film): 3650–3150, 3120 cm$^{-1}$ m/e No M+, 196, 171, 168, 150, 109, 99, 88

Analysis $C_{14}H_{27}N_3O$ requires C,66.36; H,10.74; N,16.58%. found C,66.69; H,10.46; N,15.9%.

EXAMPLE 22

This Example illustrates the preparation of the p-toluene sulphonate salt of compound No. 2 of Table I.

A solution of compound No. 2 (0.15 g, 0.63 mmol) and p-toluene sulphonic acid (0.124 g) in ethyl acetate (5 ml) and ethanol (5 ml) was heated under reflux for 6 hours. The reaction mixture was concentrated in vacuo, triturated with diethyl ether and evaporated to dryness to give the salt as a low melting off-white solid.

NMR ($CDCl_3$, 270 MHz) 0.8 (3H,t); 0.98 (9H,s); 1.0–1.4 (8H,cmplx); 2.36 (3H,s); 4.5 (2H,q); 7.2 (2H,d); 7.76 (2H,d); 8.4 (1H,s); 10.1 (1H,bs)

EXAMPLE 23

The ortho phosphoric acid salt of compound No. 2 of Table I was prepared in a manner corresponding to that of Example 20 and was characterised as follows:

NMR $CDCl_3$, 270 MHz): 0.8 (3H,t); 0.98 (9H,s); 1.0–1.6 (8H,cmplx); 4.3 (2H,q); 6.96 (4H,very broad singlet); 7.88 (1H,s); 8.33 (1H,s)

EXAMPLE 24

The dodecyl benzene sulphonic acid salt of compound No. 2 of Table I was prepared in a manner corresponding to that of Example 20 and was characterised as follows:

NMR ($CDCl_3$, 270 Mhz) 0.8 (10H,cmplx); 0.96 (9H,s); 1.2 (22H,cmplx); 1.5 (4H,cmplx); 4.5 (2H,q); 7.15 (2H,d); 7.8 (2H,d); 8.28 (1H,s); 9.85 (1H,s)

EXAMPLE 25

Whole Plant Screen (1)

Compound numbers 1–6, 9 and 10 of Table I were tested on the whole plant screen. The use of whole plant in this context refers to entire plants as opposed to a partial screen or an enzyme screen. The compounds were tested for plant growth regulator activity against up to twelve plant species for various growth effects relevant to plant growth regulation.

Methodology

The plant species used in this screen are presented in Table III, with the leaf stage at which they are sprayed. Each chemical was applied at 4000 ppm (4 kg/ha in a 1000 l/ha field volume) using a tracksprayer and a SS8004E (Teejet) nozzle.

After spray, the plants were grown in a glasshouse with 25° C. day/22° C. night temperatures and supplementary lighting was supplied when necessary (from mercury vapour lamps), to provide a 16 hour photoperiod. The exception to this were the temperate cereals, wheat and barley, which were grown in 16° C. day/13° C. night temperatures.

After 2–3 weeks in the glasshouse, depending on the time of the year, the plants were visually assessed for morphological characteristics. Formulations blanks were used as controls to assess the plants. The results are presented in Table IV.

TABLE III

| | PLANT MATERIAL USED FOR WHOLE PLANT SCREEN | | | |
|---|---|---|---|---|
| Species | Code | Variety | Growth Stage at Treatment | No. Plants per 3" Pot | Compost Type |
| Barley | BR | Atem | 1–1.5 leaves | 4 | JIP* or PEAT |
| Wheat | WW | Timmo | 1–1.5 leaves | 4 | JIP OR PEAT |

TABLE III-continued

PLANT MATERIAL USED FOR WHOLE PLANT SCREEN

| Species | Code | Variety | Growth Stage at Treatment | No. Plants per 3" Pot | Compost Type |
|---|---|---|---|---|---|
| Maize | MZ | Earliking | 2¼ leaves | 1 | PEAT |
| Vines | VN | Ohanez + unspecified | 4 leaves | 1 | PEAT |
| Soya | SY | Amsoy | 1st trifoliate | 1 | JIP |
| Tomato | TO | Ailsa Craig | 1.5–2 leaves | 1 | PEAT |
| Lettuce | LT | Verpia | 3–4 leaves | 1 | PEAT |
| Sugar beet | SB | Amono | 2 leaves | 1 | PEAT |
| *Agrostis tenius* | AT | | cut to 2 cm 48 hours before treatment | Grown in rows in plastic punnets | PEAT |
| *Cynosurus cristatus* | CC | | | | |
| *Dacrylis glomerata* | DA | | | | |
| Radish | RA | Istar | seeds | 4 | PEAT |

JIP* = John Innes Potting Compost.

TABLE IV

| COMPOUND NO. | WW | BR | MZ | AT | CC | DA | SY | SB | TO | VN | RA | LT |
|---|---|---|---|---|---|---|---|---|---|---|---|---|
| 1 | 3 | 2T | | 2 | 2 | 2 | | 3G | 3G | — | | 3G |
| 2 | 3GT | 3GT | 2G | 3G | 3G | 2 | 2GA | 3GA | 3GA | 2GAT | — | 2G |
| 3 | 3GT | 1G | 2 | 1 | 1 | | 3GA | 3GA | 3GA | 2GAT | — | 1 |
| 4 | 2G | 1GT | 2A | 2 | 3 | 2 | 2G | 3GA | 3GAT | 2GA | 3G | |
| 5 | 1T | | | 2 | 2 | 1 | 3G | 1G | 3GAT | 3A | — | 1 |
| 6 | | | 1 | G | G | | 2G | 1 | 2GT | 2GAT | — | 1 |
| 9 | 2GT | 1T | 1 | 1 | 1 | 1 | 2GAT | 2GA | 2G | G | — | 1GT |
| 10 | 3GT | 2GT | 1 | 3G | 3G | 1 | 3GAT | 2G | 2GT | 2GT | — | 3G |

Key:
Retardation 1–3 where 1 = 10–30% retardation
2 = 21–60% retardation
3 = 61–100% retardation
Greening effect = G
Apical damage = A
Tillering or side shooting = T
Blank means less than 10% effect.
— indicates that the compound was not tested against this species.

EXAMPLE 26

Whole Plant Screen (2)

Compound numbers indicated in Table VI were tested on an alternative whole plant screen (2). The compounds were tested for plant growth regulator activity against five species for various growth effects relevant to plant growth regulation.

Methodology

The plant species used in this screen are presented in Table V with the leaf stage at which they were sprayed. Each chemical was applied at 4000 ppm (4 kg/ha in a 1000 l/ha field volume) using a tracksprayer and a SS8004E (Teejet) nozzle.

After spray the plants were grown in a glasshouse with 25° C. day/22° C. night temperatures and supplementary lighting was supplied when necessary (from mercury vapour lamps), to provide a 16 hour photoperiod. The exception to this were the temperate cereals, wheat and barley which were grown in 16° C. day/13° C. night temperatures.

After 2–6 weeks in the glasshouse, depending on the time of year, the plants were visually assessed for morphological characteristics. Formulation blanks were used as controls to assess the plants. The results are presented in Table VI.

TABLE V

PLANT MATERIAL USED FOR WHOLE PLANT SCREEN (2)

| Species | Code | Variety | Growth Stage at Treatment | No. Plants per 3" Pot | Compost Type |
|---|---|---|---|---|---|
| Barley | BR | Atem | 1–1.5 leaves | 4 | JIP* |
| Wheat | WW | Timmo | 1–1.5 leaves | 4 | JIP |
| Maize | MZ | Earliking | 2¼ leaves | 1 | PEAT |
| Apple | AP | Red Delicious | 4–5 leaves | 1 | JIP |
| Rice | RC | Ishikari | 2–2¼ leaves | 4 | JIP |

JIP* = John Innes Potting Compost.

TABLE VI

| SPECIES | COMPOUND NO. | R | G | A | T | I |
|---|---|---|---|---|---|---|
| BR | 11 | 3 | 1 | | 3 | 3 |
| | 8 | 2 | 1 | | | 3 |
| | 7 | 2 | 1 | | | 3 |
| | 12 | 2 | 1 | | 1 | 3 |
| | 13 | 2 | | | | 3 |
| | 15 | 2 | | | | 2 |
| | 16 | 2 | 2 | | 2 | 3 |
| | 19 | 2 | | | | 2 |
| | 22 | 1 | | | | 1 |
| WW | 11 | 3 | 2 | | 3 | 3 |
| | 8 | 2 | 2 | | 1 | 3 |
| | 7 | 2 | 2 | | 1 | 3 |
| | 12 | 2 | 1 | | 1 | 3 |
| | 13 | 2 | 2 | | 2 | 3 |
| | 15 | 2 | 1 | | 1 | 3 |
| | 16 | 3 | 2 | | 2 | 3 |
| | 19 | 2 | 1 | | | 2 |
| | 20 | 2 | | | 3 | 2 |
| | 21 | 2 | | | | 2 |
| | 22 | 1 | | | | 2 |
| | 23 | 1 | 1 | | | 1 |

TABLE VI-continued

| SPECIES | COMPOUND NO. | R | G | A | T | I |
|---------|--------------|---|---|---|---|---|
| MZ | 11 | | | | | |
| | 8 | | | | | |
| | 7 | 1 | | | | 1 |
| | 12 | 1 | 2 | | | |
| | 16 | 1 | | | | 1 |
| | 21 | | 1 | | | |
| | 23 | 1 | | | | |
| RC | 11 | 3 | 1 | | | 3 |
| | 8 | 3 | | | 1 | 3 |
| | 7 | 2 | | | 2 | 3 |
| | 12 | 2 | 1 | | 3 | 3 |
| | 13 | 2 | 1 | | 1 | 2 |
| | 16 | 2 | | | | 3 |
| | 19 | 1 | | | | 2 |
| | 20 | | | | 1 | |
| | 21 | 2 | | | | 2 |
| | 22 | 1 | 1 | | | 1 |
| AP | 11 | 1 | | | | 1 |
| | 8 | .3 | 2 | | | 3 |
| | 7 | 2 | 1 | | | 2 |
| | 12 | 3 | 1 | 1 | 2 | 3 |
| | 13 | | | | | 1 |
| | 16 | 3 | 1 | | | 3 |
| | 19 | 3 | 1 | 3 | 2 | 3 |
| | 20 | 2 | | | | 3 |
| | 21 | 2 | 1 | 2 | 1 | 2 |
| | 22 | 2 | | | | 2 |
| | 23 | 1 | | | | 1 |

Key:
R = Retardation
G = Greening effect
A = Apical damage
T = Tillering or side shooting
I = Interligular or internodal length reduction
All effects are scored visually on a 1-3 basis where
1 = 10-30%
2 = 31-60%
3 = 61-100%
Blank means less than 10% effect.

EXAMPLE 27

Intermediate Retardant Test

Methodology

Three species are involved in this test RICE, SPRING-BARLEY and APPLES. The variety and growth stages at spray are outlined in Table VII. Compounds were applied at 1000 ppm and 4000 ppm respectively (1 kg and 4 kg ha$^{-1}$ at a field volume of 1000 l ha$^{-1}$) as an overall spray. This gives a foliar and root component in the test, i.e. this test will detect the activity of both root and foliar acting compounds. The rice was grown in 4" 'paddy' pots, i.e. the roots and bottom of the stems are immersed in water under conditions corresponding to those in paddy fields. Spring barley and apples were grown in 4" pots. The plants were assessed for height to top-most ligule at approximately 28 days after treatment for spring barley and rice and for height to apex at approximately 28 days after the treatment for apples. The results are presented in Tables VIII to X. In each case the result for the 1000 ppm and 4000 ppm test for each compound is compared to the height of the formulation blank in that test, presented as a percentage reduction in height compared to the formulation blank.

TABLE VII

PLANT MATERIAL FOR INTERMEDIATE RETARDANT TEST

| Species | Variety | Growth Stage at Treatment | No. Plants per 4" Pot | Compost Type |
|---------|---------|---------------------------|----------------------|--------------|
| Spring Barley | Atem | 3 leaves | 4 | JIP 1 |
| Rice | Ishikari | 3–4 leaves | 2 | SM2:JIP 1 |
| Apples | Red Delicious | 5–10 cm high | 1 | SM2:JIP 1 |

JIP 1 = John Innes Potting Compost.
SM2 = a mixture of loam and grit.

TABLE VIII

Percentage Reduction in Height of Apples.
(Compared to formulation blank).

| | Rate | |
|---|---|---|
| COMPOUND NO. | 1000 ppm | 4000 ppm |
| 1 | 9.5 | 61.1 |
| 2 | 31.5 | 56.2 |
| 3 | 0.7 | — |
| 4 | 8.9 | 45.2 |
| 5 | 19.5 | 57.7 |
| 6 | 22.6 | 54.1 |
| 7 | 5.3 | 21.8 |
| 8 | 13.1 | 34.9 |
| 9 | 13.6 | 28.5 |
| 10 | 23.0 | 35.3 |
| 11 | 29.8 | 34.6 |
| 12 | 35.3 | 64.8 |
| 13 | 34.8 | 44.1 |
| 14 | 60.4* | 74.7** |
| 15 | | 26.4** |
| 16 | 16.0* | 59.3** |
| 19 | 44.0 | 69.0 |
| 21 | 8.6 | 42.1 |
| 22 | 30.3 | 51.3 |
| 23 | 58.6 | 66.1 |

*500 ppm
**2000 ppm

TABLE IX

Percentage Reduction in Height of Spring Barley.
(Compared to formulation blank).

| | Rate | |
|---|---|---|
| COMPOUND NO. | 1000 ppm | 4000 ppm |
| 1 | 20.8 | 50.9 |
| 2 | 30.2 | 66.0 |
| 3 | 4.4 | 20.9 |
| 4 | 14.5 | 62.7 |
| 5 | 3.9 | 8.1 |
| 6 | 18.7 | 53.4 |
| 9 | 8.7 | 31.7 |
| 10 | 36.0 | 67.9 |
| 11 | 48.0 | 76.2 |
| 12 | 20.0 | 62.0 |
| 13 | 16.1 | 53.6 |
| 14 | 11.0 | 24.0 |
| 16 | 24.0* | 46** |
| 19 | 12.0 | 40.0 |
| 21 | 18.0 | 34.0 |
| 22 | | 11.4 |
| 23 | | 23.3 |

*500 ppm
**2000 ppm

TABLE X

Percentage Reduction in Height of Rice.
(Compared to formulation blank).

| | Rate | |
|---|---|---|
| COMPOUND NO. | 1000 ppm | 4000 ppm |
| 1 | 15.9 | — |
| 2 | 29.3 | 50.9 |
| 3 | 11.7 | 25.4 |

TABLE X-continued

Percentage Reduction in Height of Rice.
(Compared to formulation blank).

| COMPOUND NO. | Rate 1000 ppm | Rate 4000 ppm |
|---|---|---|
| 4 | 21.3 | 43.1 |
| 5 | 0.6 | 20.1 |
| 6 | 20.4 | 44.3 |
| 9 | 20.3 | 40.2 |
| 10 | 40.9 | 55.0 |
| 11 | 39.4 | 52.1 |
| 12 | 26.0 | 40.0 |
| 13 | 26.3 | 49.6 |
| 14 | 18.0 | 36.0 |
| 16 | 34.0* | 58.0* |
| 19 | 14.0 | 40.0 |
| 21 | 4.0 | 17.0 |
| 22 | 18.2 | 35.5 |
| 23 | 20.2 | 40.5 |

*500 ppm
*2000 ppm

The following Example is a general indicative comparison of compounds from EP 52424 with compounds of the present invention. The compounds have not been side-by-side tested in this example because of the large numbers involved but the retardant activity can be compared using a standard which has been on each test.

EXAMPLE 28

The compounds which are compared in this Example have been tested on one of two tests. These are whole plant screen (1) and whole plant screen (2), the methods for which are described in Examples 25 and 26 respectively.

An across-screen comparison between compounds is made by expressing the total retardation (i.e. the sum of retardation scores recorded for each species tested) caused by the compound as a percentage of the total retardation caused by the standard in that test. The standard chemical gives a measure of the performance of the test and environmental factors. By expressing the test compound activity as a percentage of the standard compound activity these factors can be eliminated. The same standard compound has been used in every test and this is paclobutrazol a proprietory growth regulator. The results are presented in Tables XI and XII.

Whilst the present example demonstrates generally that the compounds of the present invention are clearly superior plant growth regulators, in order to investigate the activity in more detail, further side-by-side comparison tests are given in the following Examples. The Examples compare representative compounds of EP 52424 with representative compounds of the present invention.

TABLE XI.

Total Retardation caused by compounds of Table I
expressed as a percentage of the total retardation caused
by paclobutrazol.

| Compound No. | % of paclo-butrazol | Cpd. No. | % of paclo-butrazol | Cpd. No. | % of paclo-butrazol |
|---|---|---|---|---|---|
| 1 | 55.6 | 7 | 150.0 | 13 | 50.0 |
| 2 | 100.0 | 8 | 166.7 | | |
| 3 | 71.4 | 9 | 60.9 | | |
| 4 | 75.8 | 10 | 86.2 | | |
| 5 | 68.0 | 11 | 76.9 | 19 | 200.0 |
| 6 | 39.1 | 12 | 91.7 | 21 | 60.0 |

TABLE XII.

Total Retardation caused by compounds of Table
I of EP 52424 expressed as a percentage of the total
retardation caused by paclobutrazol. (* = mean of 2 tests)

| Compound No. | % of paclo-butrazol | Cpd. No. | % of paclo-butrazol | Cpd. No. | % of paclo-butrazol |
|---|---|---|---|---|---|
| 1 | 21.9 | 23 | 36.1* | 43 | 71.1 |
| 2 | 43.1 | 24 | 7.1 | 44 | 33.3 |
| 8 | 18.8 | 25 | 7.1 | 45 | 25.0 |
| 9 | 18.8 | 26 | 20.1* | 48 | 0 |
| 11 | 21.9 | 29 | 29.0* | 49 | 3.6 |
| 12 | 62.5 | 32 | 25.0 | 50 | 3.6 |
| 14 | 31.3 | 33 | 7.1 | 51 | 32.1 |
| 15 | 37.5 | 36 | 3.6 | 52 | 50.0 |
| 16 | 44.4 | 37 | 7.1 | 53 | 30.3 |
| 17 | 28.1 | 38 | 0 | 55 | 21.9 |
| 19 | 18.8 | 40 | 13.9 | | |
| 20 | 7.1 | 41 | 50.0 | | |
| 21 | 7.1 | 42 | 25.0 | | |
| 22 | 47.5 | | | | |

The following Examples 29 and 30 use whole plant screen (2) and the intermediate Retardant test to compare representative compounds from the present invention with representative compounds of EP 52424.

EXAMPLE 29

Whole Plant Screen (2)

Compound numbers 2, 8 and 12 (of the present invention) were tested against compounds A, B and C of EP 52424 on whole plant screen (2). The compounds were tested for plant growth regulator activity against five species for various growth effects relevant to plant growth regulation. The structures are set out in FIG. 1.

Methodology

The plant species used in this screen are presented in Table V with the leaf stage at which they were sprayed. Each chemical was applied at 4000 ppm (4 kg/ha in a 1000 l/ha field volume) using a tracksprayer and a SS8004E (Teejet) nozzle.

After spray the plants were grown in a glasshouse with 25° C. day/22° C. night temperatures and supplementary lighting was supplied when necessary (from mercury vapour lamps), to provide a 16 hour photoperiod. The exception to this were the temperate cereals, wheat and barley which were grown in 16° C. day/13° C. night temperatures.

After 2–6 weeks in the glasshouse, depending on the time of year, the plants were visually assessed for morphological characteristics. Formulation blanks were used as controls to assess the plants. The results are presented in Table XIII.

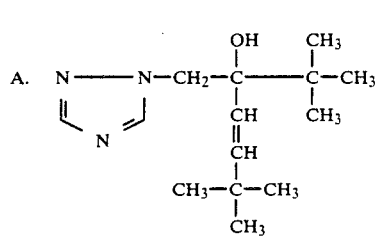

Compound No. 12
EP 0052424

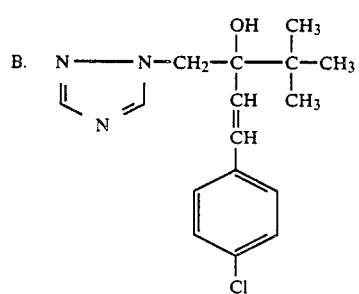

Compound No. 2
EP 0052424

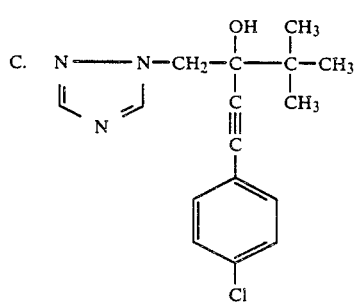

Compound No. 24
EP 0052424

FIG. 1

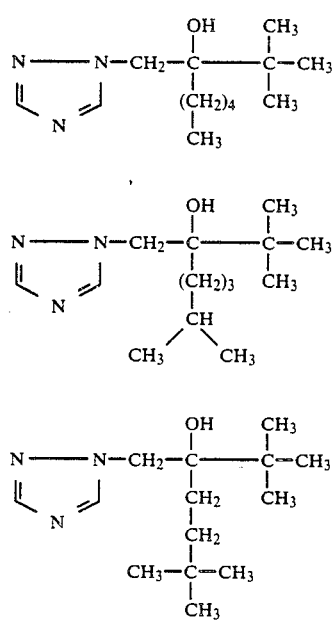

Compound No. 2 (of Table I)

Compound No. 8 (of Table I)

Compound No. 12 (of Table I)

TABLE XIII

| SPECIES | COMPOUND NO. | R | G | A | T | I |
|---|---|---|---|---|---|---|
| BR | 12 | 2 | 1 |  | 1 | 3 |
|  | 2 | 2 | 2 |  | 1 | 3 |
|  | 8 | 2 |  |  | 1 | 3 |
|  | A | 1 |  |  |  |  |
|  | B | 1 | 1 |  | 1 |  |
| WW | 12 | 2 | 1 |  | 1 | 3 |
|  | 2 | 2 |  |  | 2 | 3 |
|  | 8 | 2 | 1 |  | 2 | 3 |
|  | A | 2 | 1 |  |  | 2 |
|  | B | 2 |  |  |  | 3 |
| MZ | 12 | 1 |  |  |  |  |
|  | 2 |  |  |  |  |  |
|  | 8 | 2 |  |  |  | 2 |
|  | A | 1 |  |  |  | 1 |

TABLE XIII-continued

| SPECIES | COMPOUND NO. | R | G | A | T | I |
|---|---|---|---|---|---|---|
|  | B | 1 |  |  |  | 1 |
| RC | 12 | 2 | 1 |  | 3 | 3 |
|  | 2 | 3 | 1 |  | 2 | 3 |
|  | 8 | 3 | 1 |  | 3 | 3 |
|  | A |  |  |  | 2 |  |
|  | B | 1 |  |  |  | 1 |
| AP | 12 | 3 | 1 |  | 2 | 3 |
|  | 2 | 3 | 1 |  |  | 3 |
|  | 8 | 3 | 1 |  | 3 | 3 |
|  | A | 1 | 1 |  |  | 1 |
|  | B | 2 | 1 |  |  | 1 |

Key:
R = Retardation
G = Greening effect
A = Apical damage
T = Tillering or side shooting
I = Interligular or internodal length reduction
All effects are scored visually on a 1-3 basis where
1 = 10-30%
2 = 31-60%
3 = 61-100%
Blank means less than 10% effect.

EXAMPLE 30

Intermediate Retardant Test

Methodology

Three species are involved in this test RICE, SPRING-BARLEY and APPLES. The variety and growth stages at spray are outlined in Table VIII. Compounds were applied at 1000 ppm and 4000 ppm respectively (1 kg and 4 kg ha$^{-1}$ at a field volume of 1000 lha$^{-1}$) as an overall spray. This gives a foliar and root component in the test, i.e. this test will detect the activity of both root and foliar acting compounds. The rice was grown in 4" 'paddy' pots, i.e. the roots and bottom of the stems are immersed in water under conditions corresponding to those in paddy fields. Spring barley and apples were grown in 4" pots. The plants were assessed for height to top-most ligule at approximately 28 days after treatment for spring barley and rice and for height to apex at approximately 28 days after the treatment for apples. The results are presented in Tables XIV to XVI. In each case the result for the 1000 ppm and 4000 ppm test for each compound is compared to the height of the formulation blank in that test, presented as a percentage reduction in height compared to the formulation blank.

TABLE XIV

Percentage Reduction in Height of Apples.
(Compared to formulation blank).

| COMPOUND NO. | Rate | |
|---|---|---|
|  | 1000 ppm | 4000 ppm |
| 12 | 35 | 65 |
| 2 | 25 | 57 |
| 8 | 47 | 64 |
| A | 2 | 14 |
| B | 0 | 3 |
| C | 0 | 0 |

TABLE XV

Percentage Reduction in Height of Rice.
(Compared to formulation blank).

| COMPOUND NO. | Rate | |
|---|---|---|
|  | 1000 ppm | 4000 ppm |
| 12 | 26 | 40 |
| 2 | 28 | 52 |
| 8 | 36 | 60 |

TABLE XV-continued

Percentage Reduction in Height of Rice.
(Compared to formulation blank).

| COMPOUND NO. | Rate | |
|---|---|---|
| | 1000 ppm | 4000 ppm |
| A | 4 | 20 |
| B | 3 | 11 |
| C | 5 | 13 |

TABLE XVI

Percentage Reduction in Height of Spring Barley
(Compared to formulation blank).

| COMPOUND NO. | Rate | |
|---|---|---|
| | 1000 ppm | 4000 ppm |
| 12 | 20 | 62 |
| 2 | 30 | 65 |
| 8 | 35 | 68 |
| A | 5 | 13 |
| B | 8 | 7 |
| C | 4 | 6 |

EXAMPLE 31

This Example illustrates the activity of salts of compound No. 2 of Table I on apples in a pot test. The salts are designated by the letter given in Table II.

Methodology Young apple plants of variety Red delicious were selected for uniformity of size and leaf area. At approximately 4 leaves or 5–10 cms the plants were sprayed with the test compounds using a tracksprayer. The compounds were applied at 1000 ppm and 4000 ppm respectively (1 kg and 4 kg ha$^{-1}$ at a field volume of 1000 1 ha$^{-1}$) as an overall spray which gives a root and foliar component i.e. this test will detect the activity of both root and foliar activity compounds. The apples were grown in 4" pots in a mixture of John Innes potting compost 1, loam and grit. After treatment the plants were assessed for height to apex at 14 days and 21 days after treatment. The results are compared to the formulation blank in the test and presented as a percentage reduction in height compared to the formulation blank in Table XVII.

TABLE XVII

Percentage Reduction in height of Apples
(Compared to the formulation blank)

| Salt | 1000 ppm | | 4000 ppm | |
|---|---|---|---|---|
| | 14 DAT | 21 DAT | 14 DAT | 21 DAT |
| 2A | 21.1 | 15.2 | 36.0 | 31.6 |
| 2B | 20.2 | 7.6 | 36.8 | 28.4 |
| 2C | 13.2 | 6.3 | 35.1 | 24.7 |
| 2D | 13.2 | 3.2 | 32.5 | 22.8 |
| 2E | 21.9 | 11.4 | 36.8 | 32.3 |

EXAMPLE 32 this Example uses compound No. 2 of Table I to illustrate activity as an abscision agent for fruit thinning purposes on peaches.

Methodology

Branches of peach trees were selected for uniformity, having 20 flowers per branch. The branches were sprayed with the chemical at two rates and two timings. The rates were 250 ppm and 1000 ppm and the timings were 20% petal fall (TI) and 8 mm ovule length (T2). There were 4 replicates (i.e. branches) per treatment. The fruit thinning activity was assessed by counting the number of fruit remaining on the branch at the time when hand thinning would normally be carried out. The results are averaged and presented in Table XVIII along with the effect of the formulation blank (FB) for comparison.

TABLE XVIII

| Compound No. | Rate (ppm) | Number of fruit remaining out of 20 | |
|---|---|---|---|
| | | T1 | T2 |
| 2 | 250 | 12.37 | 6.75 |
| | 100 | 2.63 | 6.00 |
| FB* | | 9.08 | |

The manner in which the compounds of the present invention may be formulated into compositions suitable for application is shown generally in the following indicative illustrations numbered as Examples 16 to 25.

EXAMPLE 33

An emulsifiable concentrate is made up by mixing the following ingredients, and stirring the mixture until all the constituents were dissolved.

| | |
|---|---|
| Compound of Table I | 10% |
| Calcium dodecylbenzensulphate | 5% |
| "SYNPERONIC" NP13 | 5% |
| "Aromasol" H | 80% |

EXAMPLE 34

A composition in the form of grains readily dispersible in a liquid, e.g. water, is prepared by grinding together the first three ingredients in the presence of added water and then mixing in the sodium acetate. The resultant mixture is dried and passed through a British Standard mesh sieve, size 44–100, to obtain the desired size of grains.

| | |
|---|---|
| Compound of Table I | 50% |
| "Dispersol" T | 25% |
| 'SYNPERONIC" NP5 | 1.5% |
| Sodium acetate | 23.5% |

EXAMPLE 35

The following ingredients are ground together to produce a powder formulation readily dispersible in liquids.

| | |
|---|---|
| Compound of Table I | 45% |
| "Dispersol" T | 5% |
| "SYNPERONIC" NX | 0.5% |
| "Cellofas" B600 | 2% |
| China Clay GTY powder | 47.5% |

EXAMPLE 36

The active ingredient is dissolved in acetone and the resultant liquid is sprayed on to the granules of attapulgite clay. The solvent is then allowed to evaporate to produce a granular composition.

| | |
|---|---|
| Compound of Table I | 5% |
| Attapulgite granules | 95% |

EXAMPLE 37

A composition suitable for use as a seed dressing is prepared by mixing the three ingredients.

| | |
|---|---|
| Compound of Table I | 50% |
| Mineral oil | 2% |
| China clay | 48% |

EXAMPLE 38

A dusting powder is prepared by mixing the active ingredient with talc.

| | |
|---|---|
| Compound of Table I | 5% |
| Talc | 95% |

EXAMPLE 39

A flowable formulation is prepared by bead-milling the constituents set out below and then forming an aqueous suspension of the ground mixture with water.

| | |
|---|---|
| Compound of Table I | 40% |
| "Dispersol" T | 4% |
| "SYNPERONIC" NP5 | 1% |
| Water | 55% |

EXAMPLE 40

A dispersible powder formulation is made by mixing together the ingredients set out below and then grinding the mixture until all were thoroughly mixed.

| | |
|---|---|
| Compound of Table I | 25% |
| "Aerosol" OT/B | 2% |
| "Dispersol" A.C. | 5% |
| China clay | 28% |
| Silica | 40% |

EXAMPLE 41

This Example illustrates the preparation of a dispersible powder formulation. The ingredients are mixed and the mixture then ground in a comminution mill.

| | |
|---|---|
| Compound of Table I | 25% |
| "PERMINAL" BX | 1% |
| "Dispersol" T | 5% |
| Polyvinylpyrrolidone | 10% |
| Silica | 25% |
| China clay | 34% |

EXAMPLE 42

The ingredients set out below are formulated into dispersible powder by mixing then grinding the ingredients.

| | |
|---|---|
| Compound of Table I | 25% |
| "Aerosol" OT/B | 2% |
| "Dispersol" A | 5% |
| China clay | 68% |

In Examples 15 to 24 the proportions of the ingredients given are by weight.

There now follows an explanation of the compositions or substances represented by the various Trade Marks and Trade Names mentioned above.

"SYNPERONIC" NP13: a condensate of nonyl phenol (1 mole) with ethylene oxide (13 moles).

"AROMASOL" H: a solvent mixture of alkylbenzenes.

"DISPERSOL" T AND AC: a mixture of sodium sulphate and a condensate of formaldehyde with sodium naphthalene sulphonate.

"SYNPERONIC" NP5 a condensate of nonyl phenol (1 mole) with naphthalene oxide (5.5 moles).

CELLOFAS B600: a sodium carboxymethyl cellulose thickener.

What is claimed is:

1. A triazole derivative having the formula (I)

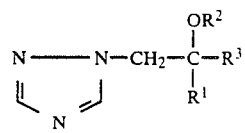

and stereoisomers thereof, wherein $R^1$ is an alkyl group containing from 4 to 9 carbon atoms, or a haloalkyl group containing from 3 to 8 carbon atoms; $R^2$ is hydrogen; and $R^3$ is a tertiary butyl group optionally substituted by halogen; and acid addition salts, and metal complexes of the compound of formula (I) wherein $R^2$ is hydrogen.

2. A triazole derivative according to claim 1 wherein $R^1$ is a branched or straight chain alkyl group containing from 4 to 7 carbon atoms or a branched or straight chain mono-haloalkyl group containing from 3 to 6 carbon atoms.

3. A triazole derivative according to claim 1 wherein $R^1$ is an alkyl group containing from 4 to 9 carbon atoms; and $R^3$ is unsubstituted tertiary butyl.

4. A plant growth regulating composition comprising an effective amount of a triazole derivative according to claim 1 and an inert carrier or diluent.

5. A method of regulating plant growth which comprises applying to the plant, or to the locus of the plant an effective amount of a triazole derivative according to claim 1.

* * * * *